(12) United States Patent
Nelms

(10) Patent No.: US 8,121,253 B2
(45) Date of Patent: Feb. 21, 2012

(54) RADIATION THERAPY USING BEAM MODIFIERS PLACED AGAINST A PATIENT'S SKIN

(75) Inventor: Benjamin E. Nelms, Merrimac, WI (US)

(73) Assignee: .Decimal, Inc., Sanford, FL (US)

( * ) Notice: Subject to any disclaimer, the term of this patent is extended or adjusted under 35 U.S.C. 154(b) by 64 days.

(21) Appl. No.: 12/695,372

(22) Filed: Jan. 28, 2010

(65) Prior Publication Data

US 2010/0195793 A1 Aug. 5, 2010

Related U.S. Application Data

(60) Provisional application No. 61/148,115, filed on Jan. 29, 2009.

(51) Int. Cl.
*A61N 5/04* (2006.01)

(52) U.S. Cl. ..... 378/65; 378/156; 250/492.3; 250/505.1

(58) Field of Classification Search .................... 378/65, 378/156; 250/492.1, 492.3, 505.1
See application file for complete search history.

(56) References Cited

U.S. PATENT DOCUMENTS

| | | | |
|---|---|---|---|
| 5,625,613 A | 4/1997 | Kato et al. | 369/112 |
| 6,853,702 B2 | 2/2005 | Renner | 378/65 |
| 7,202,486 B2 | 4/2007 | Gentry et al. | 250/492.1 |
| 2008/0123810 A1 | 5/2008 | Kirkpatrick et al. | 378/65 |
| 2008/0152085 A1 | 6/2008 | Saracen et al. | 378/65 |
| 2010/0070236 A1* | 3/2010 | Campana et al. | 702/167 |

OTHER PUBLICATIONS

Kudchadker, et al. *Utilization of Custom Electron bolus in Head and Neck Radiotherapy* Journal of Applied Clinical Medical Physics, vol. 4, No. 4, Fall 2003. pp. 321-333.

\* cited by examiner

*Primary Examiner* — Glen Kao
(74) *Attorney, Agent, or Firm* — Allen, Dyer, Doppelt, Milbrath & Gilchrist, P.A.

(57) ABSTRACT

A method for making a beam modifier to be used in radiation therapy includes defining a region of interest in a patient that is to receive radiation, with the region of interest being defined using an anatomy coordinate system format. Radiation treatment parameters are defined for the defined region of interest, and correspond to an initial type beam modifier to be coupled to an output of a radiation device. Design data on a beam modifier to be placed on the skin of the patient is generated, with the design data being based on the defined region of interest and the defined radiation treatment parameters for the defined region of interest. The design data is in the same anatomy coordinate system format as the defined region of interest that is to receive the radiation. The design data is treated as a new region of interest, and the radiation dosage to be applied to the new region of interest is re-calculated while taking into account the beam modifier to be placed on the skin of the patient.

23 Claims, 5 Drawing Sheets

RADIATION THERAPY USING BEAM MODIFIERS PLACED AGAINST A PATIENT'S SKIN

RELATED APPLICATIONS

This application claims the benefit of U.S. Provisional Application Ser. No. 61/148,115 filed Jan. 29, 2009, the entire contents of which are incorporated herein by reference.

FIELD OF THE INVENTION

The present invention relates to the field of radiation therapy, and in particular, to use of the radiation therapy (RT) extension of the DICOM protocol to support placement of a beam modifier on the skin of a patient receiving radiation therapy.

BACKGROUND OF THE INVENTION

Conformal radiation therapy (CRT) is a treatment method for cancer patients requiring radiation treatment. CRT is an extremely precise method of treatment delivery where the radiation dose conforms to the target and avoids the surrounding critical structures. For photon radiation, CRT is often achieved with intensity-modulated radiation therapy (IMRT), whereas for particulate therapy (electrons or protons), CRT can be achieved with custom energy/range modulators. A customized solid material compensator or beam modifier may be used to modulate the intensity of the radiation beam for the patient to achieve CRT.

The customized beam modifier 10 is typically fixed to an output of a radiation device 20 directing radiation 22 to the target area 32 on the patient 30, as illustrated in FIG. 1. The target area 32 is also known as the region of interest. The customized beam modifier 10 insures that the target 32 receives the correct radiation dose, and the healthy tissue 34 receives substantially less radiation.

A radiation treatment facility generates the data necessary for treating the patient, including the data for manufacturing the customized beam modifier 10. To provide interconnectivity for exchange of the data between different radiation devices that may be within or outside the radiation treatment facility, the DICOM (Digital Imaging and Communications in Medicine) protocol has been adopted as the standard. Since the data being exchanged is directed to radiation therapy (RT), the RT extension to the DICOM protocol is applicable.

A drawback of DICOM RT is that it is limited to the customized beam modifier 10 being fixed to the radiation device 20. In other words, the design data within DICOM RT is limited to the use of the beam modifier 10 in this configuration. As illustrated in FIG. 1, there is a gap 40 between the patient 30 receiving the radiation 22 and the customized beam modifier 20.

However, there are situations where it would be desirable to place a customized beam modifier 10 against the patient's skin. Instead of the gap 40 being between the customized beam modifier 10 and the patient 30, the gap would be between the radiation device 20 and the customized beam modifier 10. This arrangement is desirable when superficial target volumes are being treated on the patient 30. Example beam modifiers that may be placed on the patient's surface include a photon bolus, an electron bolus, and a proton range compensator.

Unfortunately, DICOM RT does not support these types of beam modifiers. Consequently, there is a need to be able to use DICOM RT to support placement of a beam modifier on the skin of a patient receiving radiation therapy.

SUMMARY OF THE INVENTION

In view of the foregoing background, it is therefore an object of the present invention to provide a method for making a beam modifier to be placed on the skin of a patient receiving radiation from a radiation device, while being compatible with the DICOM RT protocol.

This and other objects, advantages and features in accordance with the present invention are provided by operating a treatment planning system to define a region of interest in the patient that is to receive the radiation, with the region of interest being defined using an anatomy coordinate system format. The treatment planning system defines radiation treatment parameters for the defined region of interest, with the radiation treatment parameters corresponding to an initial type beam modifier intended to be coupled to an output of the radiation device. The treatment planning system may also calculate radiation dosage to be applied to the region of interest.

The method further comprises a medical device manufacturer receiving the defined and calculated information from the treatment planning system corresponding to the initial type beam modifier. The medical device manufacturer generates design data on the beam modifier that is to be placed on the skin of the patient based on the received defined and calculated information corresponding to the initial type beam modifier. The design data is in the same anatomy coordinate system format as the defined region of interest in the patient that is to receive the radiation.

The method further comprises operating the treatment planning system to receive from the medical device manufacturer the design data on the beam modifier that is to be placed on the skin of the patient, and treating the design data as a new region of interest that is to receive the radiation. The treatment planning system may then re-calculate the radiation dosage to be applied to the new region of interest while taking into account the beam modifier placed on the skin of the patient.

The above steps may be performed with a virtual beam modifier that is to be placed on the skin of the patient to receive radiation. Nonetheless, the method further comprises making the beam modifier to be placed on the skin of the patient based on the design data.

The defined and calculated information provided by the treatment planning system to the medical device manufacturer may be based on a Digital Imaging and Communications in Medicine protocol directed to Radiation Therapy (DICOM RT). Similarly, the design data on the beam modifier to be placed on the skin of the patient is also based on the DICOM RT protocol.

In particular, the DICOM RT protocol comprises a plurality of objects including an RT Structure Set. The region of interest defined by the treatment planning system is based on the RT Structure Set, and the design data on the beam modifier to be placed on the skin of the patient as generated by the medical device manufacturer is also based on RT Structure Set. Since the anatomy coordinate system is part of the DICOM RT Structure Set, data on the newly defined region of interest (which takes into account the beam modifier to be placed on the skin of the patient) can advantageously be received by the treatment planning system via the DICOM RT Structure Set.

The beam modifier to be placed on the skin of the patient may comprise a bolus. The bolus may be a photon bolus or an electron bolus, for example. In addition, the beam modifier may be a proton range compensator.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 2:
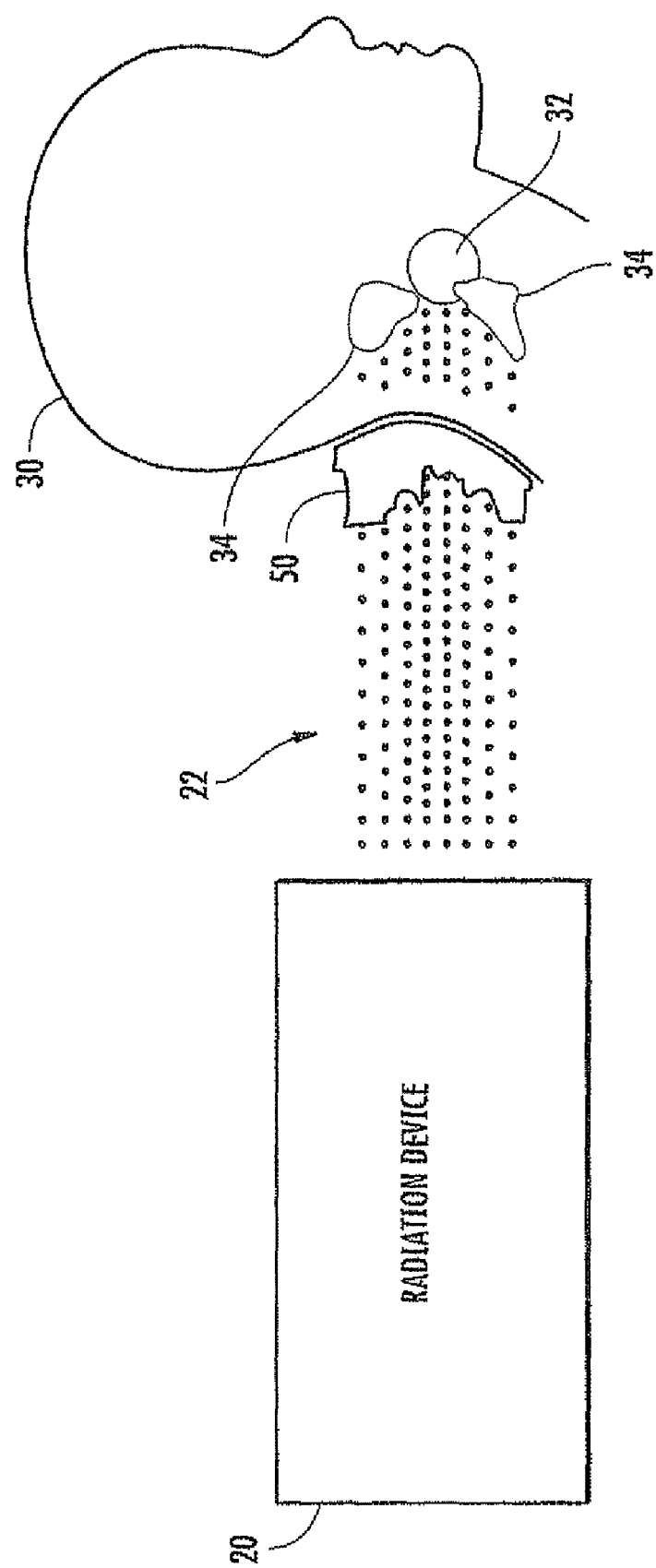
FIG. 2 is a block diagram of a beam modifier on the skin of a patient receiving radiation in accordance with the present invention.

As will be explained in greater below, the radiation therapy (RT) extension of the DICOM protocol can be used to provide placement of a beam modifier 50 on the skin of a patient 30 receiving radiation therapy, as illustrated in FIG. 2. As readily understood by those skilled in the art, DICOM RT is made up of individual objects.

Figure 1:
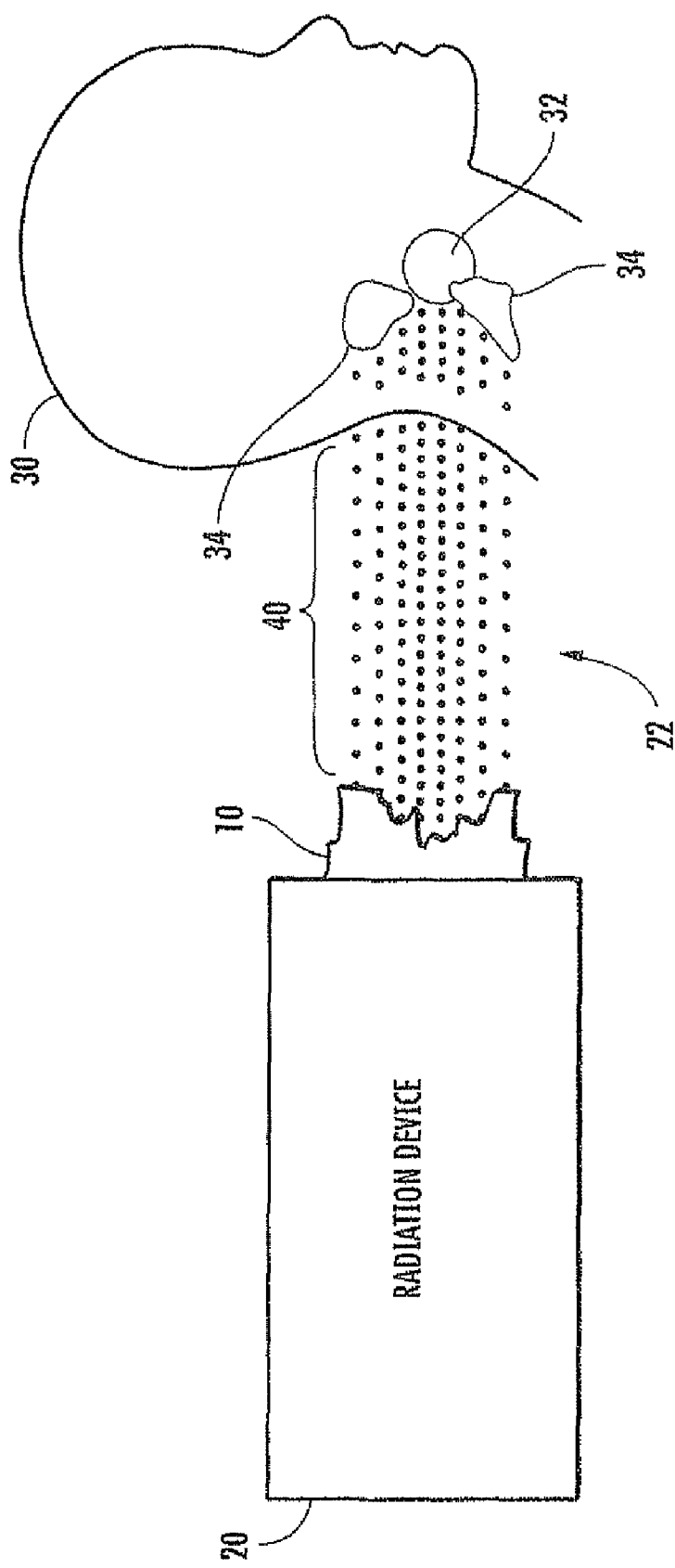
FIG. 1 is a block diagram of a beam modifier coupled to an output of a radiation device in accordance with the prior art.
Figure 3:
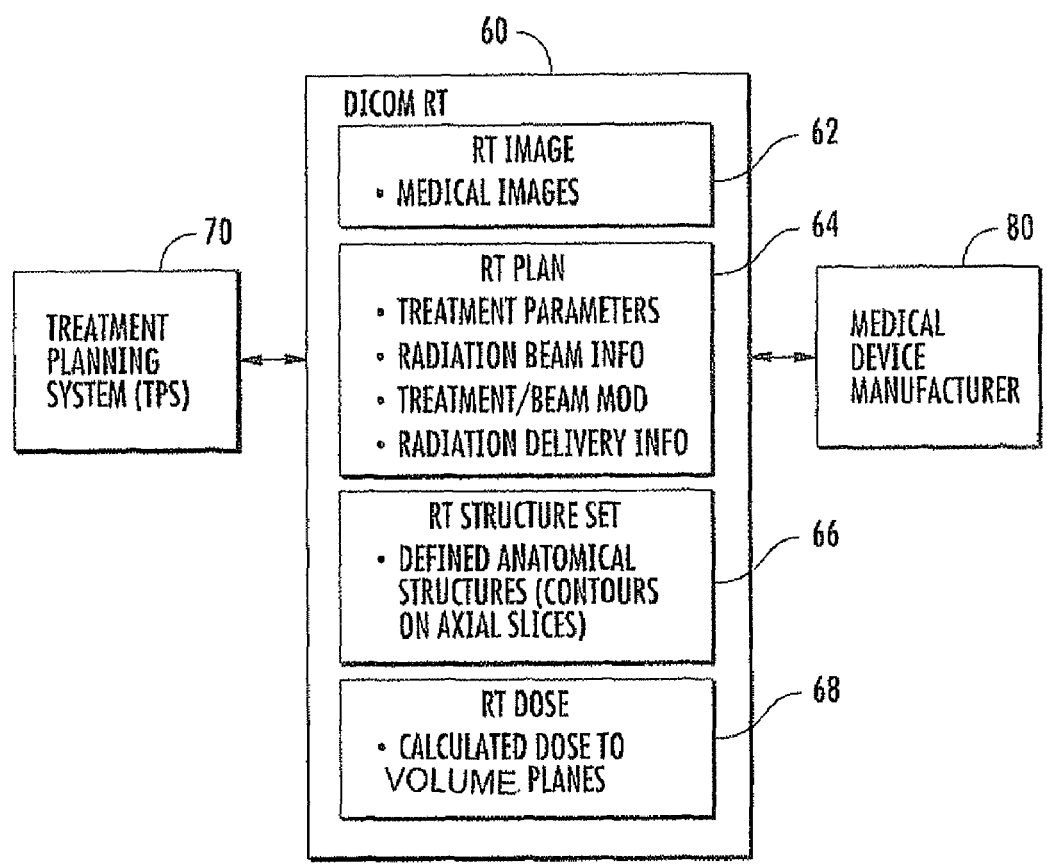
FIG. 3 is a block diagram illustrating the exchange of DICOM RT data between a treatment planning system and a medical device manufacturer in accordance with the prior art.

As illustrated in FIG. 3, the individual objects defining DICOM RT 60 include an RT Image 62, an RT Plan 64, an RT Structure Set 66 and an RT Dose 68. Radiation therapy data for the patient 30 may be exchanged between a treatment planning system (TPS) 70, and a medical device manufacturer 80 providing the beam modifier 10. However, the exchanged radiation therapy data is limited to a beam modifier 10 that is to be fixed to an output of a radiation device 20, as illustrated in FIG. 1.

The RT image 62 is directed to medical images of the patient 30 receiving radiation therapy. The RT plan 64 is directed to treatment parameters, radiation beam information, treatment/beam modifiers, radiation delivery information, etc. The DICOM RT Structure Set 66 is the defined anatomical structures, i.e., the contours on axial slices of the region of interest to receive radiation. The DICOM RT Dose 68 is directed to the calculated dose to be applied to the region of interest 32 in the patient 30.

Information necessary to design the beam modifier 10 is provided to the medical device manufacturer 80 by the treatment planning system 70. This information is in the DICOM RT Plan 64. As readily understood by those skilled in the art, all beam modifiers are currently described in the DICOM RT Plan 64. The medical device manufacturer 80 may then use custom software (p.d) to design the shape of the beam modifier 10.

However, as noted above, the beam modifier 10 is intended to be fixed to the radiation device 20. Design information on the beam modifier 10 is passed back to the treatment planning system 70 via the DICOM RT Plan 64 so that the proper radiation dose can be re-calculation. As an alternative, the design information on the beam modifier 10 may be passed back to the treatment planning system 70 via proprietary software specific (i.e., other than DICOM RT Plan 64).

In accordance with the present invention, the medical device manufacturer 80 creates the design for the beam modifier 50 that is to be placed on the skin of the patient 30 after receiving the DICOM RT Plan 64 and the DICOM RT Structure Set 66. In order to design the beam modifier 50, it is now considered a new structure functioning as a bolus, as illustrated in FIG. 2.

Ideally, data on the newly created design (i.e., beam modifier 50) as determined by the medical device manufacturer 80 would then be transferred back to the treatment planning system 70 so that the proper radiation dose could be re-calculated. The problem is that the DICOM RT Plan 64 object does not adequately account for all the design parameters for the beam modifier 50 as determined by the medical device manufacturer 80, nor does the treatment planning system 70 have the capability to process such data if provided in the DICOM RT Plan 64.

For the design data corresponding to the beam modifier 50 to be read by the treatment planning system 70, it needs to be in a format other than the DICOM RT Plan 64. This other format is advantageously based on the medical device manufacturer 80 virtually positioning the beam modifier 50 on the skin of the patient 30 as a bolus, and then treating the beam modifier 50 as a "region of interest" in the anatomy coordinate system. Since the anatomy coordinate system is part of the DICOM RT Structure Set 66 (defining the initial region of interest), data on the newly defined region of interest can be received by the treatment planning system 70 via the DICOM RT Structure Set 66.

In effect, the beam modifier 50 positioned on the skin of the patient 30 is being treated as a bolus. In radiation therapy, a bolus is a tissue equivalent substance placed on the patient's skin in order to achieve the required dose distribution to the target site and surrounding healthy tissues. Once the shape of the bolus (i.e., beam modifier 50 to be placed on the skin of the patient 30) is determined, this information is sent back to the treatment planning system 70 via the DICOM RT Structure Set 66.

The treatment planning system 70 can then re-calculate the dose for the region of interest that is to receive radiation while treating the bolus positioned on the skin of the patient 30 as the beam modifier 50. This procedure may be virtually performed without having to physically build the beam modifier and place it on the skin of the patient 30 when generating data on the new region of interest. Alternatively, the beam modifier 50 may be physically formed when generating data on the new region of interest.

The steps involved in this process include the treatment planning system 70 generating the images of the target area 34, drawing the target area on the images, and determining placement of the radiation beams on the target area. The medical device manufacturer 80 may then use custom software (p.d) to create the shape of the beam modifier 50.

As an alternative to creating an entirely new beam modifier 50 design from scratch, the medical device manufacturer 80 may modify an existing beam modifier design so that it may be placed on the skin of a patient 30, i.e., a bolus.

Figure 4:
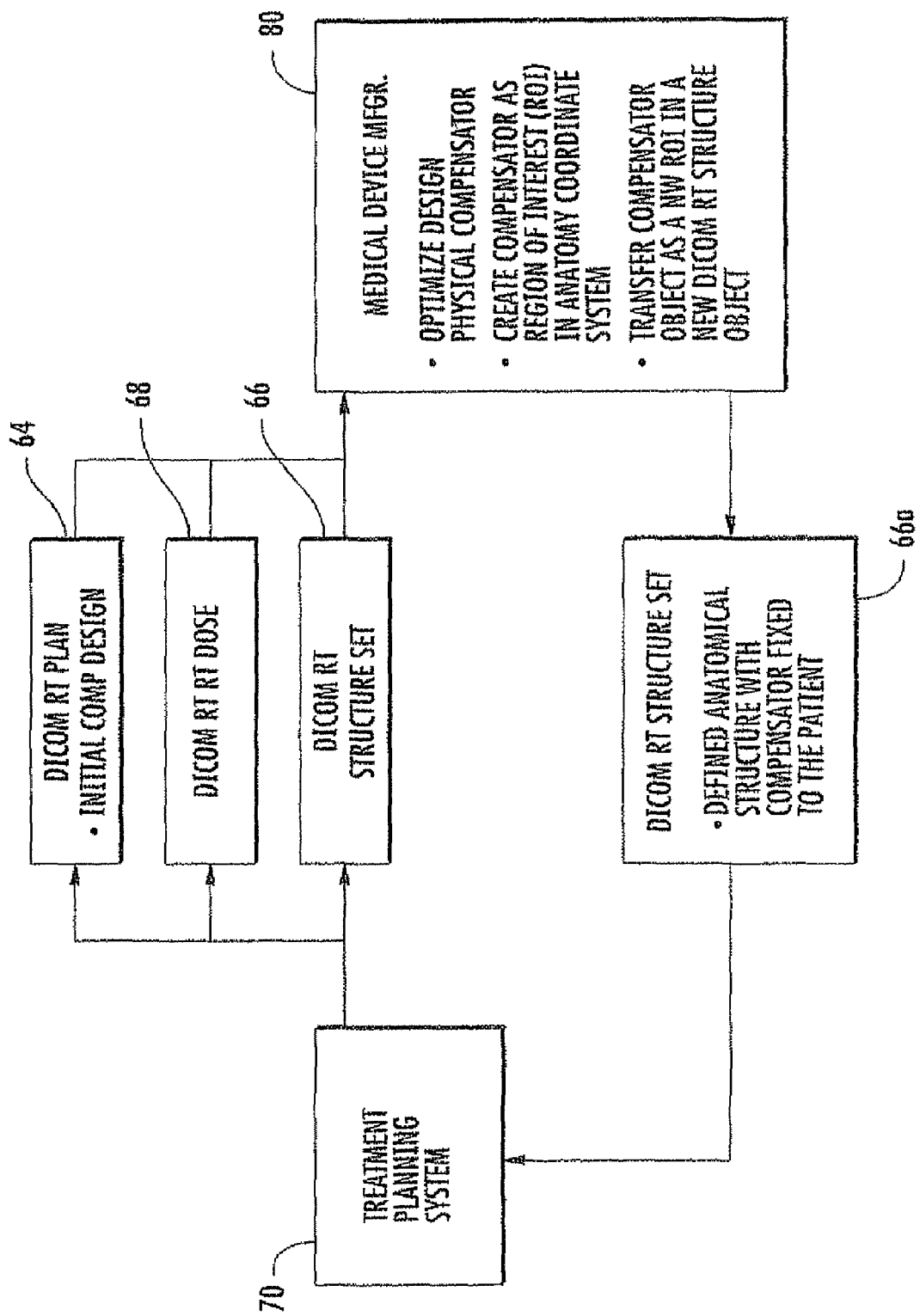
FIG. 4 is a block diagram illustrating the exchange of DICOM RT data between a treatment planning system and a medical device manufacturer in accordance with the present invention.

Referring now to FIG. 4, information in the DICOM RT Plan 64 (i.e., beam direction) and in the DICOM RT Structure Set 66 (i.e., for the target and patient anatomy volumes) is provided to the medical device manufacturer 80. The medical device manufacturer 80 uses proprietary data files to produce a three-dimensional shape (i.e., beam modifier 50). Data on the three-dimensional shape is passed back to the treatment planning system 70 via the DICOM RT Structure Set 66a so that the new data can be read and the proper radiation dose 22 for the patent 30 can be re-calculated.

In other words, for the treatment planning system 70 to be able to re-calculate the dose in view of the newly designed beam modifier 50, the medical device manufacturer 80 treats the beam modifier 50 as new region of interest on the skin of the patient 30. Data on this new region of interest may then be put in a format based on the anatomy coordinate system. This information is provided to the treatment planning system 70 via the DICOM RT Structure Set 66a. The treatment planning system 70 then re-calculates the dose in view of the data provided in the DICOM RT Structure Set 66a.

Example beam modifiers that may be placed on the skin of the patient 30 include a photon bolus, an electron bolus, and a proton range compensator. In one embodiment, the bolus may be equal thickness for a photon external beam or HDR branchytherapy.

Figure 5:
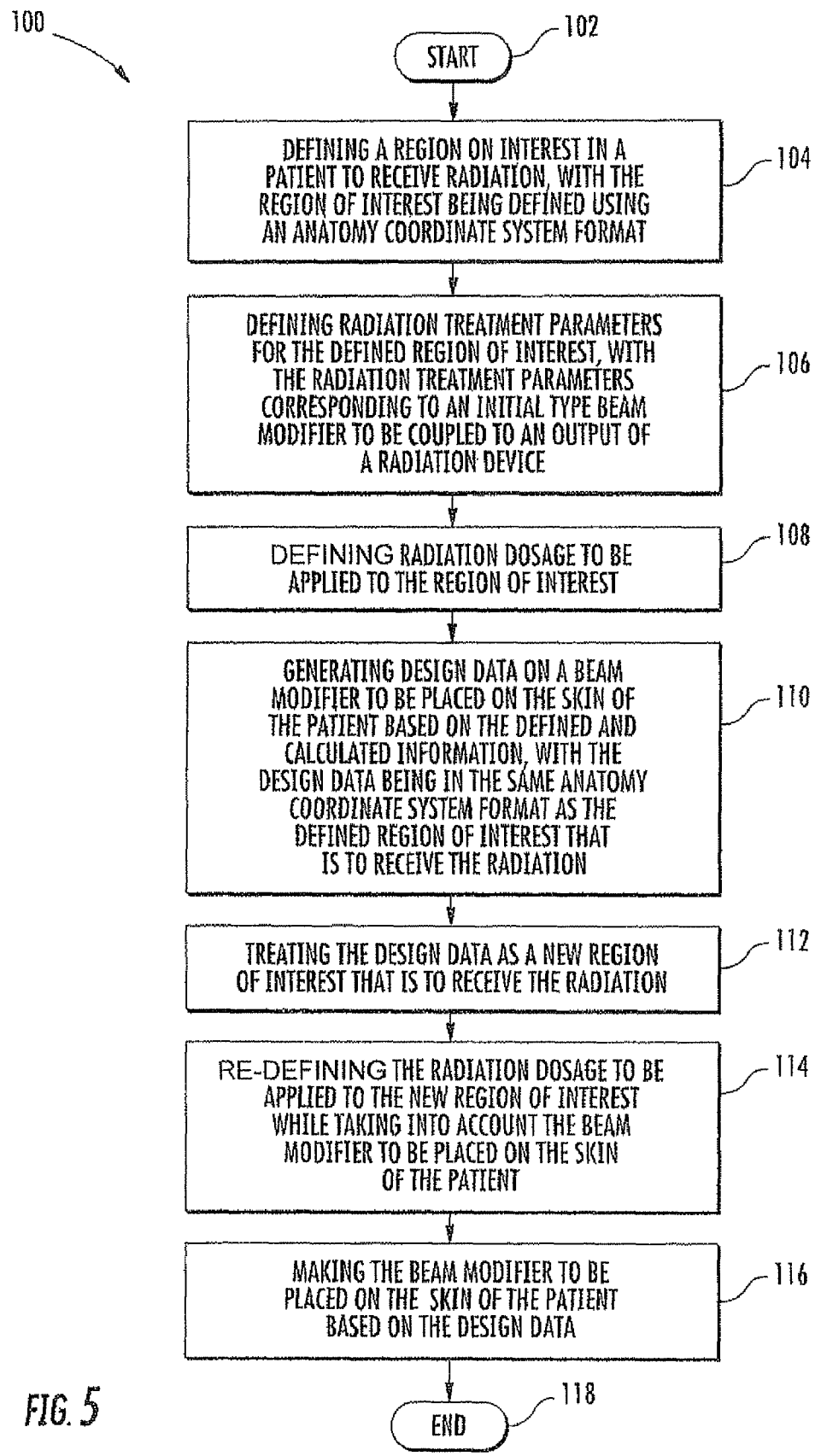
FIG. 5 is a flowchart of a method for making a beam modifier to be placed on the skin of a patient receiving radiation in accordance with the present invention.

Referring now to the flow diagram 100 in FIG. 5, a method for making a beam modifier 50 to be placed on the skin of a patient 30 receiving radiation 22 will now be discussed. From the start (Block 102), a treatment planning system 70 defines a region of interest 32 in the patient 30 to receive the radiation 22 at Block 104. The region of interest 32 is defined using an anatomy coordinate system format. The treatment planning system 70 also defines at Block 106 radiation treatment parameters for the defined region of interest 32. The radiation treatment parameters correspond to an initial type beam modifier 10 to be coupled to an output of the radiation device 20. The treatment planning system 70 also calculates or defines radiation dosage 22 to be applied to the region of interest 32 at Block 108.

A medical device manufacturer 80 receives the defined and calculated information from the treatment planning system corresponding to the initial type beam modifier 10 to be coupled to an output of the radiation device 20 at Block 110. The medical device manufacturer 80 generates design data on the beam modifier 50 to be placed on the skin of the patient 30 based on the received defined and calculated information. The design data is in the same anatomy coordinate system format as the defined region of interest 32 that is to receive the radiation 22.

The treatment planning system 70 receives from the medical device manufacturer 80 the design data on the beam modifier 50 to be placed on the skin of the patient 30. The treatment planning system 70 treats the design data as a new region of interest and structure that is to receive the radiation 22. The treatment planning system 70 also re-defines the radiation dosage 22 to be applied to the new region of interest and structure (i.e., newly augumented anatomical structure set) while taking into account the beam modifier 50 to be placed on the skin of the patient 30.

The above steps may be performed with a virtual beam modifier 50 that is to be placed on the skin of the patient 30 to receive radiation. Nonetheless, the method further comprises at Block 116 making the beam modifier 50 to be placed on the skin of the patient 30 based on the design data. The method ends at Block 118.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A method for making a beam modifier to be placed on skin of a patient and to be used in radiation therapy comprising:

defining a region of interest in a patient that is to receive radiation, with the region of interest being defined using an anatomy coordinate system format;

defining radiation treatment parameters for the defined region of interest, with the radiation treatment parameters corresponding to an initial type beam modifier to be coupled to an output of a radiation device;

defining radiation dosage to be applied to the region of interest;

generating design data on a beam modifier to be placed on the skin of the patient, the design data being based on the defined region of interest and the defined radiation treatment parameters for the defined region of interest, and with the design data being in the same anatomy coordinate system format as the defined region of interest that is to receive the radiation;

treating the design data on the beam modifier to be placed on the skin of the patient as a new region of interest and structure that the radiation will intersect;

re-defining the radiation dosage to be applied to the new region of interest and structure while taking into account the beam modifier to be placed on the skin of the patient; and making the beam modifier to be placed on the skin of the patient based on the design data.

2. The method according to claim 1 wherein the anatomy coordinate system format defines contours on axial slices of the region of interest that is to receive the radiation.

3. The method according to claim 1 wherein the design data defines a three-dimensional shape for the beam modifier to be placed on the skin of the patient.

4. The method according to claim 1 wherein the defined information provided by a treatment planning system to a medical device manufacturer is based on a Digital Imaging and Communications in Medicine protocol directed to Radiation Therapy (DICOM RT), and wherein the design data on the beam modifier to be placed on the skin of the patient provided by the medical device manufacturer to the treatment planning system is also based on the DICOM RT protocol.

5. The method according to claim 4 wherein the DICOM RT protocol comprises a plurality of objects including a DICOM RT Structure Set, with the region of interest defined by the treatment planning system being in the DICOM RT Structure Set, and with the design data on the beam modifier to be placed on the skin of the patient generated by the medical device manufacturer also being in the DICOM RT Structure Set.

6. The method according to claim 1 wherein the beam modifier to be placed on the skin of the patient comprises a bolus.

7. The method according to claim 6 wherein the bolus comprises at least one of a photon bolus and an electron bolus.

8. The method according to claim 1 wherein the beam modifier to be placed on the skin of the patient comprises proton range compensator.

9. A method for making a beam modifier to be placed on the of a patient receiving radiation from a radiation device, the method comprising:

with a treatment planning system to perform the following, defining a region of interest in the patient to receive the radiation, with the region of interest being defined using an anatomy coordinate system format, defining radiation treatment parameters for the defined region of interest, with the radiation treatment parameters corresponding to an initial type beam modifier to be coupled to an output of the radiation device, and calculating radiation dosage to be applied to the region of interest;

with a medical device manufacturer to perform the following, receiving the defined and calculated information from the treatment planning system corresponding to the initial type beam modifier to be coupled to an output of the radiation device, and generating design data on the beam modifier to be placed on the skin of the patient based on the received defined and calculated information, with the design data being in the same anatomy coordinate system format as the defined region of interest that is to receive the radiation; and with the treatment planning system to perform the following, receiving from the medical device manufacturer the design data on the beam modifier to be placed on the skin of the patient, treating the design data as a new region of interest that is to receive the radiation, and re-calculating the radiation dosage to be applied to the new region of interest while taking into account the beam modifier to be placed on the skin of the patient.

10. The method according to claim 9 further comprising the medical device manufacturer making the beam modifier to be placed on the skin of the patient based on the design data.

11. The method according to claim 9 wherein the anatomy coordinate system format defines contours on axial slices of the region of interest that is to receive the radiation.

12. The method according to claim 9 wherein the design data defines a three-dimensional shape for the beam modifier to be placed on the skin of the patient.

13. The method according to claim 9 wherein the defined information provided by the treatment planning system to the medical device manufacturer is based on a Digital Imaging and Communications in Medicine protocol directed to Radiation Therapy (DICOM RT), and wherein the design data on the beam modifier to be placed on the skin of the patient provided by the medical device manufacturer to the treatment planning system is also based on the DICOM RT protocol.

14. The method according to claim 13 wherein the DICOM RT protocol comprises a plurality of objects including a DICOM RT Structure Set, with the region of interest defined by the treatment planning system being in the DICOM RT Structure Set, and with the design data on the beam modifier to be placed on the skin of the patient generated by the medical device manufacturer also being in the DICOM RT Structure Set.

15. The method according to claim 9 wherein the beam modifier to be placed on the skin of the patient comprises a bolus.

16. The method according to claim 15 wherein the bolus comprises at least one of a photon bolus and an electron bolus.

17. The method according to claim 9 wherein the beam modifier to be placed on the skin of the patient comprises a proton range compensator.

18. A method for making a beam modifier to be placed on skin of a patient and to be used in radiation therapy in accordance with a Digital Imaging and Communications in Medicine Radiation Therapy (DICOM RT) protocol, the DICOM RT protocol comprising an RT Plan object, an RT Structure Set object and an RT Dose object, the method comprising:

defining a region of interest in a patient that is to receive radiation, with the region of interest being defined using the RT Structure Set object;

defining radiation treatment parameters for the defined region of interest, with the radiation treatment parameters corresponding to an initial type beam modifier to be coupled to an output of a radiation device and being defined using the RT Plan object;

defining radiation dosage to be applied to the region of interest using the RT Dose object;

generating design data on a beam modifier to be placed on the skin of the patient, the design data being based on the defined region of interest and the defined radiation treatment parameters for the defined region of interest, and with the design data being generated using the RT Structure Set object;

treating the design data in the ET Structure Set object on the beam modifier to be placed on the skin of the patient as a new region of interest that is to receive the radiation;

re-defining the radiation dosage to be applied to the new region of interest using the RT Dose object while taking into account the beam modifier to be placed on the skin of the patient; and making the beam modifier to be laced on the skin of the patient based on the design data.

19. The method according to claim 18 wherein the anatomy coordinate system format defines contours on axial slices of the region of interest that is to receive the radiation.

20. The method according to claim 18 wherein the design data defines a three-dimensional shape for the beam modifier to be placed on the skin of the patient.

21. The method according to claim 18 wherein the beam modifier to be placed on the skin of the patient comprises a bolus.

22. The method according to claim 21 wherein the bolus comprises at least one of a photon bolus and an electron bolus.

23. The method according to claim 18 wherein the beam modifier to be placed on the skin of the patient comprises a proton range compensator.

* * * * *